United States Patent [19]

Hofer

[11] B 4,001,353

[45] Jan. 4, 1977

[54] PREPARATION OF O,S-DIMETHYL-THIOL-PHOSPHORIC ACID DIESTER-AMIDE

[75] Inventor: Wolfgang Hofer, Wuppertal, Germany

[73] Assignee: Bayer Aktiengesellschaft, Leverkusen, Germany

[22] Filed: Mar. 27, 1974

[21] Appl. No.: 455,486

[44] Published under the second Trial Voluntary Protest Program on March 16, 1976 as document No. B 455,486.

Related U.S. Application Data

[62] Division of Ser. No. 303,302, Nov. 2, 1972, Pat. No. 3,845,170.

[30] Foreign Application Priority Data

Nov. 16, 1971 Germany .......................... 2156718

[52] U.S. Cl. .............................. 260/984; 260/959; 260/988
[51] Int. Cl.² .......................................... C07F 9/24
[58] Field of Search ................... 260/984, 988, 959

[56] References Cited

UNITED STATES PATENTS

| | | | |
|---|---|---|---|
| 2,434,357 | 1/1948 | Fischer ........................... | 260/988 X |
| 3,167,574 | 1/1965 | Brown et al. ................... | 260/988 X |

OTHER PUBLICATIONS

Kosolapoff, Organophosphorus Compounds, John Wiley & Sons, Inc., New York, (1950), p. 294.
Arbuzov et al., Bull. Acad. Sci. USSR, Div. Chem. Sci., 1954, pp. 909–912.
Houben–Weyl, Methoden des Organischen Chemie, 1964, p. 404.

*Primary Examiner*—Richard L. Raymond
*Attorney, Agent, or Firm*—Burgess, Dinklage & Sprung

[57] ABSTRACT

The new compound tetramethyl-dithiolpyrophosphoric acid ester of the formula

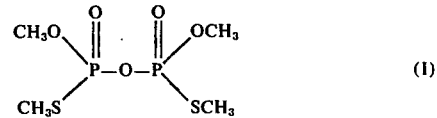

(I)

is produced by reacting phosgene with an alkali metal or ammonium salt of O,S-dimethylthiolphosphoric acid ester, preferably in a diluent. By-product chloride salt precipitates out and the solvent can be separated from the desired product or the solution can be directly reacted with ammonia to form the insecticidally active O,S-dimethylthiolphosphoric acid diester-amide.

3 Claims, No Drawings

PREPARATION OF O,S-DIMETHYL-THIOL-PHOSPHORIC ACID DIESTER-AMIDE

This is a division of application Ser. No. 303,302, filed Nov. 2, 1972, now U.S. Pat. No. 3,845,170.

The present invention relates to certain new O,O',S,S'-tetramethyldithiolpyrophosphoric acid ester, to a process for its production and to its use as intermediate in the production of certain highly active pesticidal substances, especially O,S-dimethyl-thiolphosphoric acid diester-amide which is a highly active insectide.

O,S-dimethyl-thiolphosphoric acid diester-amide is known as a highly active insecticide.

It is also known that this compound can be made from salts of O-methyl-thiolphosphoric acid ester-amide by reaction with methylating agents. However, this process suffers from the disadvantage that large amounts of solvent have to be used for the extraction of the O,S-dimethyl-thiolphosphoric acid diester-amide from water (German Patent DOS No. 1,210,835).

It is also known that O,S-dimethyl-thiolphosphoric acid diester-amide can be made from O,O-dimethyl-thiono-phosphoric acid diester-chloride and ammonia, with subsequent thermal rearrangement. In this process, the product obtained has been found not to satisfy the purity requirements of products in large-scale industrial processes (German Patent DAS No. 1,246,730).

The present invention provides O,O',S,S'-tetramethyldithiolpyrophosphoric acid ester of the formula

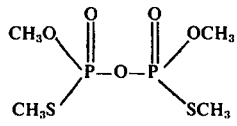

(I)

This compound has been found outstandingly suitable as an intermediate, especially for the production of O,S-dimethylthiolphosphoric acid diester-amide.

The invention also provides a process for the production of O,O',S,S'-tetramethyl-dithiolpyrophosphoric acid ester of the formula (I) in which a salt of O,S-dimethyl-thiolphosphoric acid ester of the formula

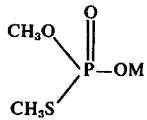

(II)

in which

M is an alkali metal or ammonium, is reacted with phosgene, optionally in the presence of a diluent.

The O,O',S,S'-tetramethyldithiolpyrophosphoric acid ester according to the invention can be reacted practically quantitatively, that is to say in yields of up to 98 percent of theory, with ammonia in an inert organic non-aqueous solvent, to give O,S-dimethyl-thiolphosphoric acid diester-amide. In carrying out this process, the salt of the O,S-dimethyl-thiolphosphoric acid ester, formed as a by-product, may be filtered off and the solvent may be stripped off in vacuo. This salt which has separated out can again be used for the preparation of the pyro-ester of formula (I). The desired O,S-dimethyl-thiolphosphoric acid diester-amide is normally left in high purity. The possibility of preparing this compound in non-aqueous solvents and the extremely simple working-up, in addition to the excellent yields and the high degree of purity, are significant advantages over the first of the two known processes mentioned above for the preparation of O,S-dimethyl-thiolphosphoric acid diester-amide, in which, preferably, the salt of the O-methylthiolphosphoric acid ester-amide is methylated in water. It is the great disadvantage of this known process that water is used as the solvent since O,S-dimethyl-thiolphosphoric acid diester-amide is very easily soluble in water and large amounts of solvent have to be used in order to extract it from the aqueous phase.

As compared to the second known process, namely the preparation of the product from O,O-dimethyl-thionophosphoric acid diester-chloride and ammonia with subsequent thermal rearrangement, the product obtained via the pyro-ester is distinguished by greater purity.

Since, in addition to the synthesis of new active substances in the field of pesticides, it is also of great economic importance to provide new intermediates, which can readily be manufactured industrially, for the synthesis of active substances which are already known and proven, the product according to the invention represents a genuine enrichment of the art.

The course of the reaction for the production of the compound according to the invention can be represented by the following equation:

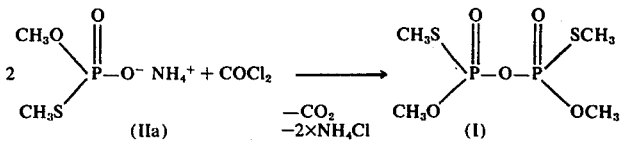

The starting substances defined by the formula (II) can readily be produced, even on an industrial scale, for example by reacting the very cheap and readily accessible dimethylphosphite with sulfur and ammonia or reacting trimethyl-thionophosphoric acid ester with aqueous bases, for example ammonia or sodium hydroxide solution, and thermally rearranging the products obtained.

The reaction according to the invention is preferably carried out in the presence of a diluent. As such it is possible to employ practically all inert organic solvents. Preferred solvents include aliphatic and aromatic hydrocarbons, which may be chlorinated, such as benzene, toluene, xylene. benzine, methylene chloride, chloroform, carbon tetrachloride and chlorobenzene, ketones, for example acetone, methyl ethyl ketone, methyl iso-propyl ketone and methyl iso-butyl ketone, and nitriles, such as acetonitrile and propionitrile.

The reaction temperature can be varied over a wide range. In general the reaction is carried out at about 10° to 90°C, preferably about 20° to 60°C.

The reaction is generally carried out at normal pressure.

In carrying out the process, 1,3 moles of phosgene may be introduced at room temperature into 2 moles of the salt of the phosphoric acid ester in one of the solvents indicated; in the course of which the temperature of the reaction mixture rises. After continuous stirring for one or more hours, the ammonium or alkali metal chloride which has separated out may be filtered off and the solvent may be stripped off. If the O,O',S,S'-tetramethyldithiolpyrophosphoric acid ester is immediately to be processed further, an intermediate isolation is not necessary and instead the solution freed from the salt which has separated out can be directly reacted further.

The substance according to the invention is obtained in the form of a colorless oil which is characterized by its refractive index. The NMR-spectrum also serves for further identification. It shows that an optical isomer mixture is present. As has already been mentioned, O,O',S,S'-tetramethyldithiolpyrophosphoric acid ester produced is a new intermediate product for the synthesis of the O,S-dimethyl-thiolphosphoric acid diester-amide known as an insecticide.

The invention is illustrated by the following Example.

EXAMPLE

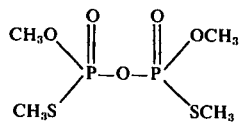

(I)

130 g (1.32 moles) of phosgene were introduced over the course of approximately 2 hours into a suspension of 318 g (2 moles) of the ammonium salt of O,S-dimethylthiolphosphoric acid diester in 700 ml of 1,2-dichloroethane at room temperature, while stirring, in the course of which the temperature of the reaction solution rose to 50°C with vigorous evolution of carbon dioxide. After stirring for a further hour, the ammonium chloride which had precipitated was filtered off and the solvent was distilled off in vacuo. 263 g (98 percent of theory) of O,O',S,S'-tetramethyldithiolpyrophosphoric acid ester remained as a colorless oil of refractive index $n_D^{25}$: 1.4935.

Analysis: calculated for $C_4H_{12}O_5P_2S_2$ (266):24.1%,S; 23.3%, P. found: 24.3%, S; 22.9%, P.

b. Alternatively, after removing the ammonium chloride precipitate, ammonia was bubbled into the filtrate until it was no longer consumed. The precipitate of O,S-dimethylthiolphosphoric acid diester ammonium salt was filtered off. The solvent was distilled off from the filtrate in vacuo leaving an almost quantitative yield of substantially pure O,S-dimethylthiolphosphoric acid diester-amide.

It will be appreciated that the instant specification and examples are set forth by way of illustration and not limitation and that various modifications and changes may be made without departing from the spirit and scope of the present invention.

What is claimed is:

1. A process for the production of O,S-dimethyl-thiol-phosphoric acid diesteramide of the formula

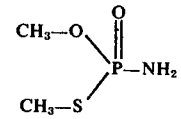

which comprises reacting about 1.3 moles of phosgene with about 2 moles of a salt of O,S-dimethyl-thiolphosphoric acid ester of the formula

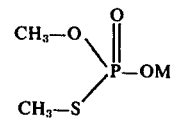

in which
M is an alkali metal of ammonium,
at about 20° to 60°C in the presence of a diluent to form tetramethyl-dithiolpyrophosphoric acid ester of the formula

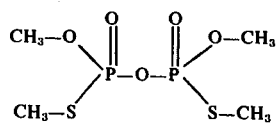

and contacting the tetramethyl-dithiolpyrophosphoric acid ester in an inert diluent with ammonia.

2. A process according to claim 1 in which the phosgene is introduced at room temperature into the salt of O,S-dimethylthiolphosphoric acid ester in a diluent, and after continuous stirring for at least about one hour the chloride formed is filtered off from the diluent having the ester dissolved therein.

3. A process according to claim 1 including the further step of filtering off by-product ammonium salt, and removing the solvent from the filtrate leaving substantially pure O,S-dimethyl-thiol-phosphoric acid diester-amide.

* * * * *